US009370367B2

(12) United States Patent
Mozdzierz

(10) Patent No.: US 9,370,367 B2
(45) Date of Patent: Jun. 21, 2016

(54) CIRCULAR STAPLER WITH CONTROLLED TISSUE COMPRESSION

(71) Applicant: Covidien LP, Mansfield, MA (US)

(72) Inventor: Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 470 days.

(21) Appl. No.: 13/947,287

(22) Filed: Jul. 22, 2013

(65) Prior Publication Data
US 2013/0299553 A1 Nov. 14, 2013

Related U.S. Application Data

(62) Division of application No. 13/097,242, filed on Apr. 29, 2011, now Pat. No. 8,490,850.

(51) Int. Cl.
*A61B 17/068* (2006.01)
*A61B 17/115* (2006.01)

(52) U.S. Cl.
CPC .................................. *A61B 17/1155* (2013.01)

(58) Field of Classification Search
CPC ............. A61B 17/0644; A61B 17/068; B25B 23/141; F16D 7/06
USPC .......... 227/175.1, 176.1, 179.1, 180.1, 181.1; 173/170, 178
See application file for complete search history.

(56) References Cited

U.S. PATENT DOCUMENTS

| | | |
|---|---|---|
| 3,205,985 A | 9/1965 | Pearl |
| 3,942,337 A * | 3/1976 | Leonard ................ B25B 23/141 464/36 |
| 4,473,077 A | 9/1984 | Noiles et al. |
| 4,576,167 A | 3/1986 | Noiles |
| 4,646,745 A | 3/1987 | Noiles |
| 5,005,749 A | 4/1991 | Aranyi |
| 5,119,983 A | 6/1992 | Green et al. |
| 5,346,022 A | 9/1994 | Krivec |
| 5,433,665 A | 7/1995 | Beaty et al. |
| 5,588,579 A | 12/1996 | Schnut et al. |
| 5,776,155 A | 7/1998 | Beaupre et al. |
| 6,053,390 A | 4/2000 | Green et al. |

(Continued)

FOREIGN PATENT DOCUMENTS

| | | |
|---|---|---|
| WO | 2008/039270 A1 | 4/2008 |
| WO | 2008038249 A2 | 4/2008 |
| WO | WO 2009/039506 | 3/2009 |

OTHER PUBLICATIONS

Australian Examination Report for Australian Patent Application No. 2014202901 dated Apr. 16, 2015.

(Continued)

*Primary Examiner* — Nathaniel Chukwurah

(57) ABSTRACT

There are provided torque limiting mechanisms for use in tissue clamping surgical instruments. The torque limiting mechanisms generally include a driven member, engageable with an approximating mechanism of the surgical instruments, and having a driven surface and a driving member having a driving surface engageable with the driven surface of the driven member. The driving member is rotatable relative to the driven member such that the driving surface of the driving member slips relative to or dissengages from the driven surface of the driven member at a predetermined engagement pressure.

7 Claims, 6 Drawing Sheets

(56) References Cited

U.S. PATENT DOCUMENTS

| | | | |
|---|---|---|---|
| 6,129,735 A | 10/2000 | Okada et al. | |
| 6,132,435 A * | 10/2000 | Young | A61B 17/8875 192/56.54 |
| 6,793,652 B1 | 9/2004 | Whitman et al. | |
| 7,032,798 B2 | 4/2006 | Whitman et al. | |
| 7,197,848 B2 | 4/2007 | Vaccari et al. | |
| 7,243,581 B1 | 7/2007 | Gao | |
| 7,303,106 B2 | 12/2007 | Milliman et al. | |
| 7,467,576 B2 | 12/2008 | Gao | |
| 7,506,791 B2 * | 3/2009 | Omaits | A61B 17/0644 227/175.1 |
| 7,922,063 B2 | 4/2011 | Zemlok et al. | |
| 2005/0145402 A1 | 7/2005 | Hehli et al. | |
| 2005/0165403 A1 | 7/2005 | Miller | |
| 2009/0209990 A1 | 8/2009 | Yates et al. | |
| 2009/0283642 A1 * | 11/2009 | Gemmati | B64C 13/24 244/178 |
| 2011/0017801 A1 | 1/2011 | Zemlok et al. | |
| 2011/0139851 A1 | 6/2011 | McCuen | |

OTHER PUBLICATIONS

European Search Report for EP 12165923 dated Nov. 5, 2014.

European Examination Report for EP 12 165 923.9 dated Jan. 4, 2016.

Japanese Office Action mailed Feb. 5, 2016 in corresponding Japanese Patent Application No. 2012-084048.

* cited by examiner

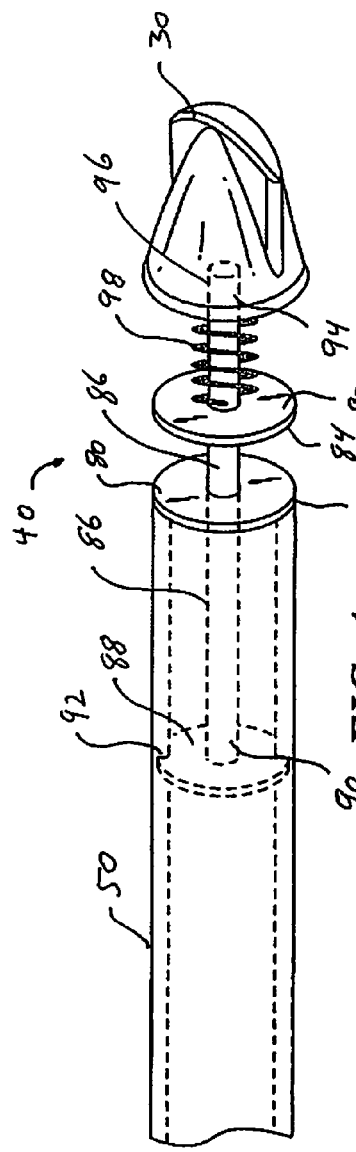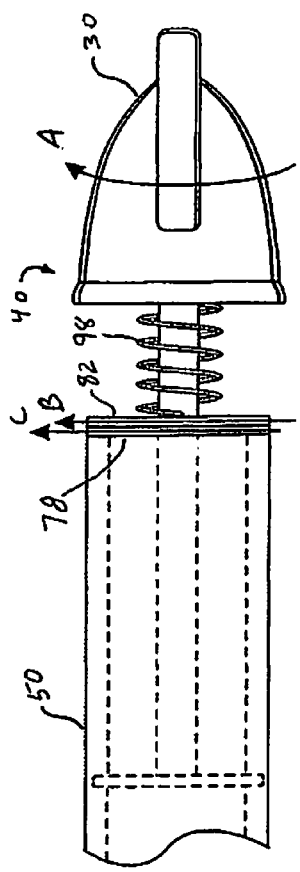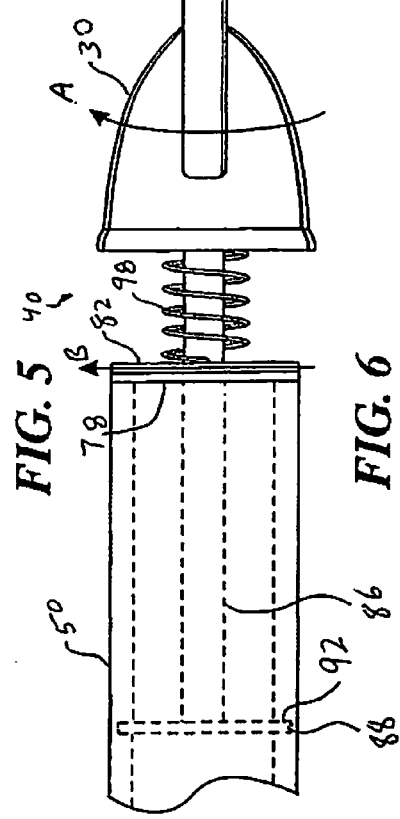

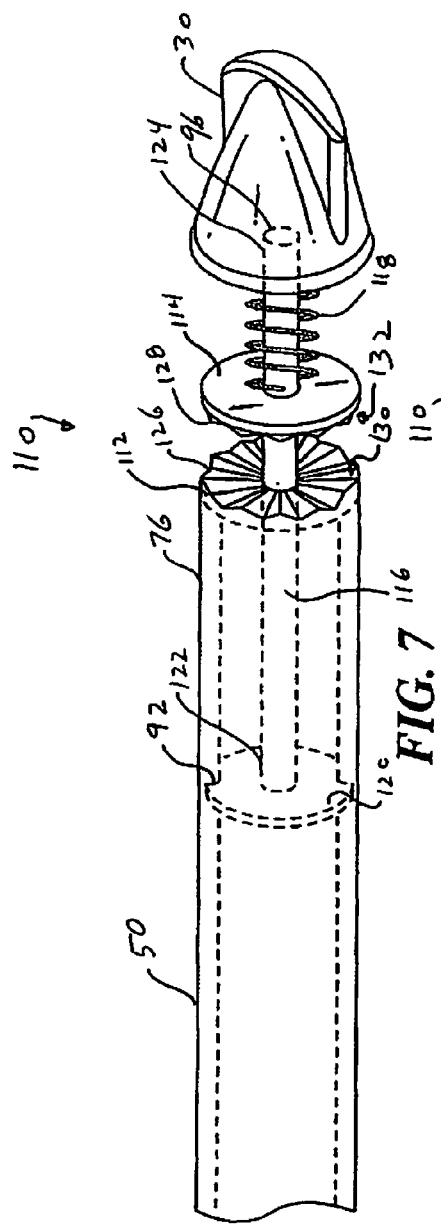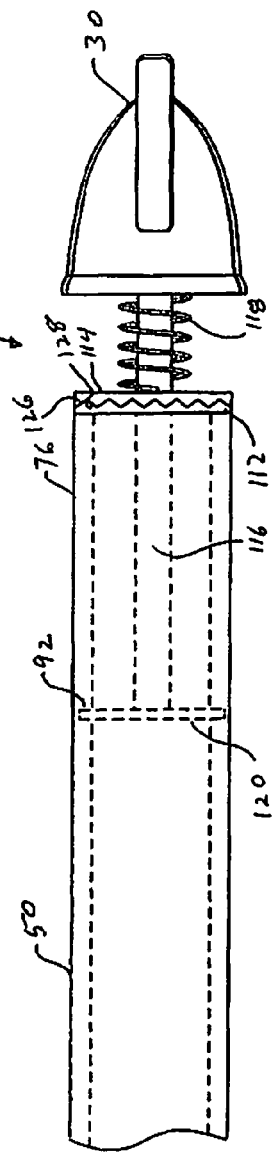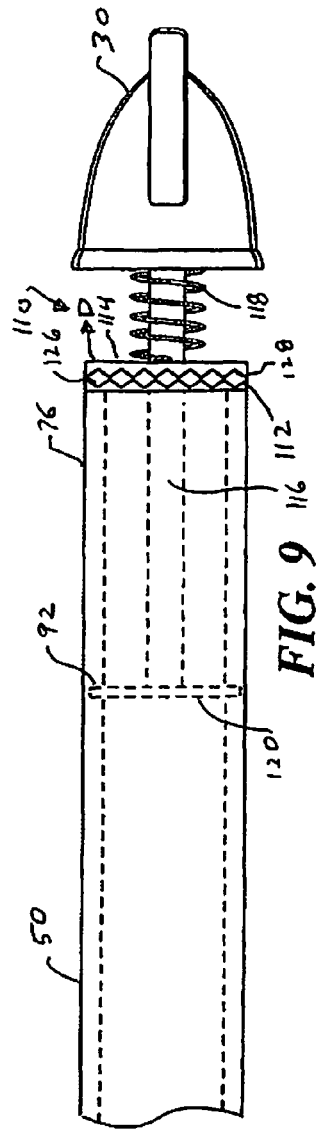

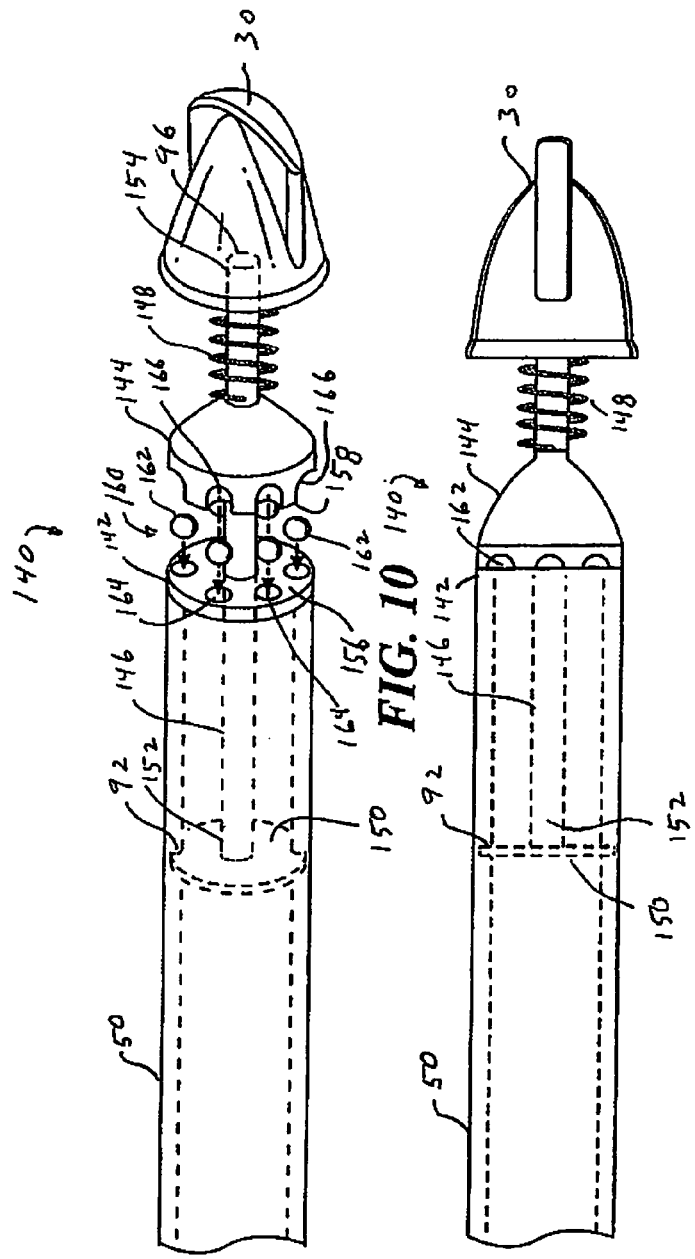
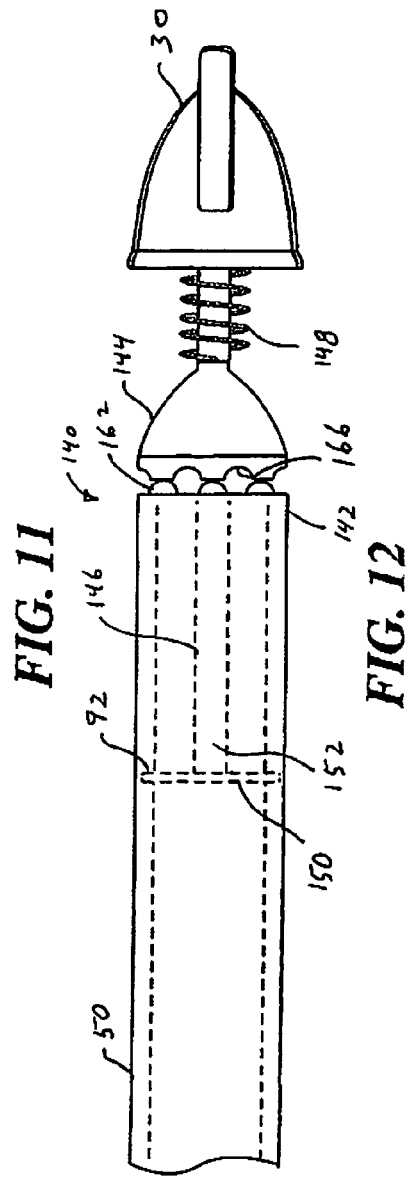
FIG. 10　FIG. 11　FIG. 12

CIRCULAR STAPLER WITH CONTROLLED TISSUE COMPRESSION

CROSS-REFERENCE TO RELATED APPLICATION

This application is a divisional of U.S. patent application Ser. No. 13/097,242, filed Apr. 29, 2011, the entire contents of which are incorporated herein by reference.

BACKGROUND

1. Technical Field

The present disclosure relates to a force limiting mechanism for use with surgical instruments incorporating tissue clamping structure. More particularly, the present disclosure relates to tissue compression limiting mechanisms for use in surgical stapling instruments.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 7,303,106, 6,053,390, 5,588,579, 5,119,983, 5,005,749, 4,646,745, 4,576,167 and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end adjacent the staple holding component. Opposing end portions of tissue of the organs to be stapled are clamped between the anvil head and the staple holding component. The clamped tissue is stapled by driving a plurality of staples from the staple holding component so that the ends of the staples pass through the tissue and are deformed by the anvil head.

In use, the staple holding component and anvil assembly are positioned within opposed tissue sections of the organs to be joined and are approximated to pull the opposed tissue sections into position for stapling. This compresses the opposed tissues sections together. Current devices rely upon the operator to compress the tissue sections until the instrument reaches a set approximation. If reaching the set approximation compresses the tissue excessively then tissue damage or restricted blood flow may lead to tissue necrosis. If the tissue is not clamped with sufficient compression, there is a greater propensity for bleeding and/or leaks at the anastomotic joint.

Therefore, there exists a need for a surgical stapler with a compression limiting mechanism to prevent excessive tissue compression. There further exists a need for a surgical stapling instrument having a user selectable compression limiting mechanism to allow the user to preselect the amount of compression applied to the tissue sections.

SUMMARY

There is provided a force or torque limiting mechanism for use in a surgical instrument. The torque limiting mechanism generally includes a driven member, engageable with an approximating mechanism of the surgical instrument, and having a driven surface; and a driving member having a driving surface engageable with the driven surface of the driven member. The driving member is connected to the clamping actuator of the instrument. The driving surface of the driving member slips relative to the driven surface of the driven member at a predetermined engagement pressure. The mechanism has a torque control with a member that adjusts the pressure applied by the driving member to the driven member.

In certain preferred embodiments, the driving member is rotatable relative to the driven member. The driving surface can frictionally engage the driven surface. In certain embodiments, the driving surface and the driven surface have interengaging structure. In a specific embodiment, the driving surface and the driven surface have interengaging teeth.

In a further alternative embodiment, the interengaging structure is a detent mechanism. The detent mechanism includes at least one movable connector positioned between the driving surface and the driven surface. In a more specific embodiment, at least one of the driving surface and driven surface includes cups and the other of the driving surface and driven surface supports balls removably engageable with the cups.

The disclosed torque limiting mechanism further includes a spring engageable with the driving member such that the driving member is spring biased into engagement with the driven member.

A torque control is provided and is engageable with the biasing spring to preset the amount of pressure applied by the biasing spring to the driving member. The torque control includes a hook engageable with the biasing spring and a slide member.

There is also provided a surgical instrument including a body portion, a first clamping member mounted on the body portion and a second clamping member movable relative to the first clamping member. An approximating mechanism is provided for moving the second clamping member relative to the first clamping member. The approximating mechanism includes a longitudinally movable drive screw having a helical groove formed therein and a rotatable sleeve mounted about the drive screw. The rotatable sleeve includes a drive pin extending into the helical groove such that rotation of the rotatable sleeve longitudinally translates the drive screw within the body portion.

A torque limiting mechanism is provided within the body portion and is engageable with the rotatable sleeve such that at least a portion of the torque limiting mechanism slips relative to the rotatable sleeve at a predetermined engagement pressure. The torque limiting mechanism includes a driven surface affixed to the rotatable sleeve and a driving surface engageable with the driven surface.

In one embodiment, the driving surface frictionally engages the driven surface. In an alternative embodiment, the driving surface and the driven surface have interengaging structure. In a specific embodiment, the driving surface and the driven surface have interengaging teeth.

In a further alternative embodiment, the interengaging structure is a detent mechanism, wherein at least one of the driving surface and driven surface includes cups and the other of the driving surface and driven surface supports balls removably engageable with the cups.

The surgical instrument further includes a spring engageable with the driving member. The driving member is spring biased into engagement with the driven member.

There is further disclosed a method of preventing over compression of tissue between first and second clamping members of a surgical instrument. The method includes providing a surgical instrument having a body portion, a first clamping member mounted on the body portion and a second clamping member movable relative to the first clamping member. An approximating mechanism is provided for moving the second clamping member relative to the first clamping member. The approximating mechanism includes a longitudinally movable drive screw having a helical groove formed therein and a rotatable sleeve mounted about the drive screw.

The rotatable sleeve includes a drive pin extending into the helical groove such that rotation of the rotatable sleeve longitudinally translates the drive screw within the body portion. A torque limiting mechanism is provided and is engageable with the rotatable sleeve. An approximation knob is rotationally mounted on the body portion and is engageable with the torque limiting mechanism.

The method further includes the step of rotating the approximation knob to rotate rotatable sleeve such that at least a portion of the torque limiting mechanism slips relative to the rotatable sleeve at a predetermined engagement pressure.

DESCRIPTION OF THE DRAWINGS

Various embodiments of the presently disclosed surgical stapler with a torque limiting mechanism for controlled tissue compression are disclosed herein with reference to the drawings, wherein:

FIG. 4 is a perspective view of the torque limiting mechanism of FIG. 3;

FIG. 5 is a side view of the torque limiting mechanism of FIG. 4 with friction or pressure plates engaged;

FIG. 6 is a side view similar to FIG. 5 with the friction plates slipping relative to each other;

FIG. 7 is a perspective view of an alternative embodiment of a torque limiting mechanism for use in the surgical stapler of FIG. 1;

FIG. 8 is a side view of the torque limiting mechanism of FIG. 7 with a driven plate and drive plate engaged;

FIG. 9 is a view similar to FIG. 8 with the drive and driven plates disengaged;

FIG. 10 is a perspective view of a further alternative embodiment of a torque limiting mechanism for use with the surgical stapler of FIG. 1;

FIG. 11 is a side view of the torque limiting mechanism of FIG. 10 with a driven plate and drive plate engaged; and FIG. 12 is a view similar to FIG. 11 with the drive and driven plates disengaged.

DETAILED DESCRIPTION OF EMBODIMENTS

Embodiments of the presently disclosed surgical stapling device incorporating tissue compression limiting mechanisms will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
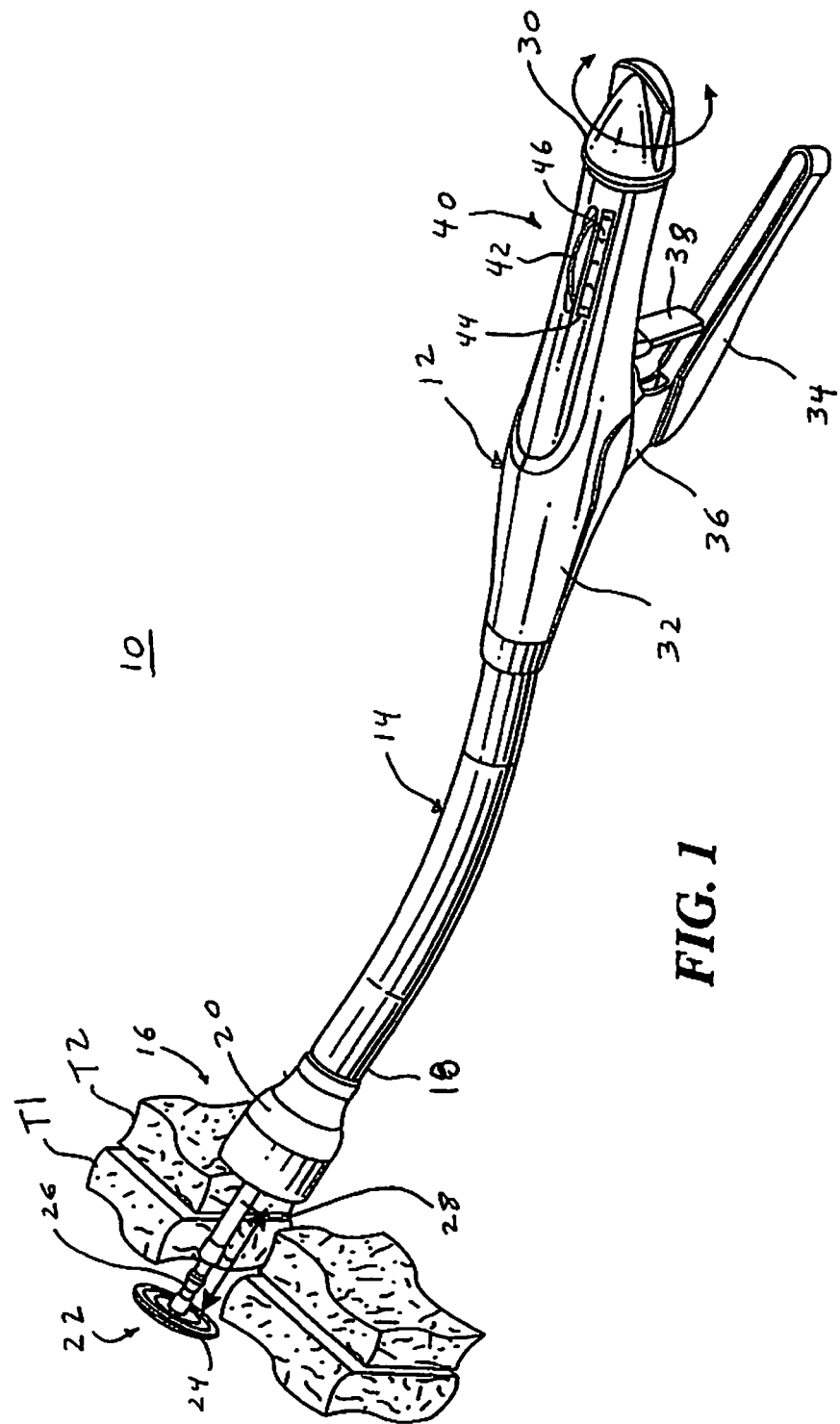
FIG. 1 is a perspective view of a surgical stapler incorporating one embodiment of a torque limiting mechanism for controlled tissue compression.

Referring initially to FIG. 1 there is disclosed a surgical stapling device 10. Surgical stapling device 10 is a circular stapler. Surgical stapling device 10 generally includes a handle assembly 12 and an elongate body portion 14 extending distally from handle assembly 12. An operable head assembly 16 is mounted on a distal end 18 of elongate body portion 14 and generally includes a staple cartridge 20 mounted to distal end 18 of elongate body portion 14 and an anvil assembly 22 which is movable relative to staple cartridge 20 in a manner described in more detail hereinbelow. Anvil assembly 22 includes an anvil plate 24 and an anvil shaft 26 extending proximally from anvil plate 24. A movable anvil retainer or retention shaft 28 extends out of distal end 18 of elongate body portion 14 and is provided to removably receive anvil shaft 26. An approximation knob 30 is rotatably mounted on a body housing 32 of handle assembly 12 and is operable to move anvil assembly 22 relative to staple cartridge 20 to grasp and compress tissue.

A trigger 34 is movably mounted to a trigger extension 36 of body housing 32. Actuation of trigger 34 functions to eject staples (not shown) out of staple cartridge 20 and into anvil plate 24. A trigger lock 38 is movably mounted on body housing 32 and is provided to block movement of trigger 34 until manually moved out of the way of trigger 34 to prevent inadvertent firing. The handle assembly and body housing may be arranged as disclosed in U.S. Pat. No. 7,303,106, the disclosure of which is hereby incorporated by reference herein, in its entirety. The '106 patent also discloses an assembly having a pusher back 186, a cylindrical knife 188 and a staple guide 192. The pusher back is connected to a pusher link 74 and has a plurality of pusher fingers for firing the surgical staples from the staple cartridge.

A torque limiting mechanism 40 is contained within body housing 32 to control the amount of compression applied to tissues captured between staple cartridge 20 and anvil plate 24. Approximation knob 30 is engageable with torque limiting mechanism 40 such that when tissues compressed between staple cartridge 20 and anvil plate 24 reach a predetermined level of compression, approximation knob 30 slips free of engagement with anvil retention shaft 28 thereby preventing any further compression to the tissue. Torque limiting mechanism 40 includes a torque control 42, extending through body housing 32, for presetting the level at which approximation knob 30 slips in a manner described hereinbelow. An indicia plate 44 is mounted on body housing 32 adjacent torque control 42 and includes numerical indicia 46 to allow the operator to preset the slip point or range of approximation knob 30. In this way, the experience of the surgeon can be used to set the instrument according to the type of tissue being stapled or clamped, the age of the patient, the condition of the tissue, or other factors.

Figure 2:
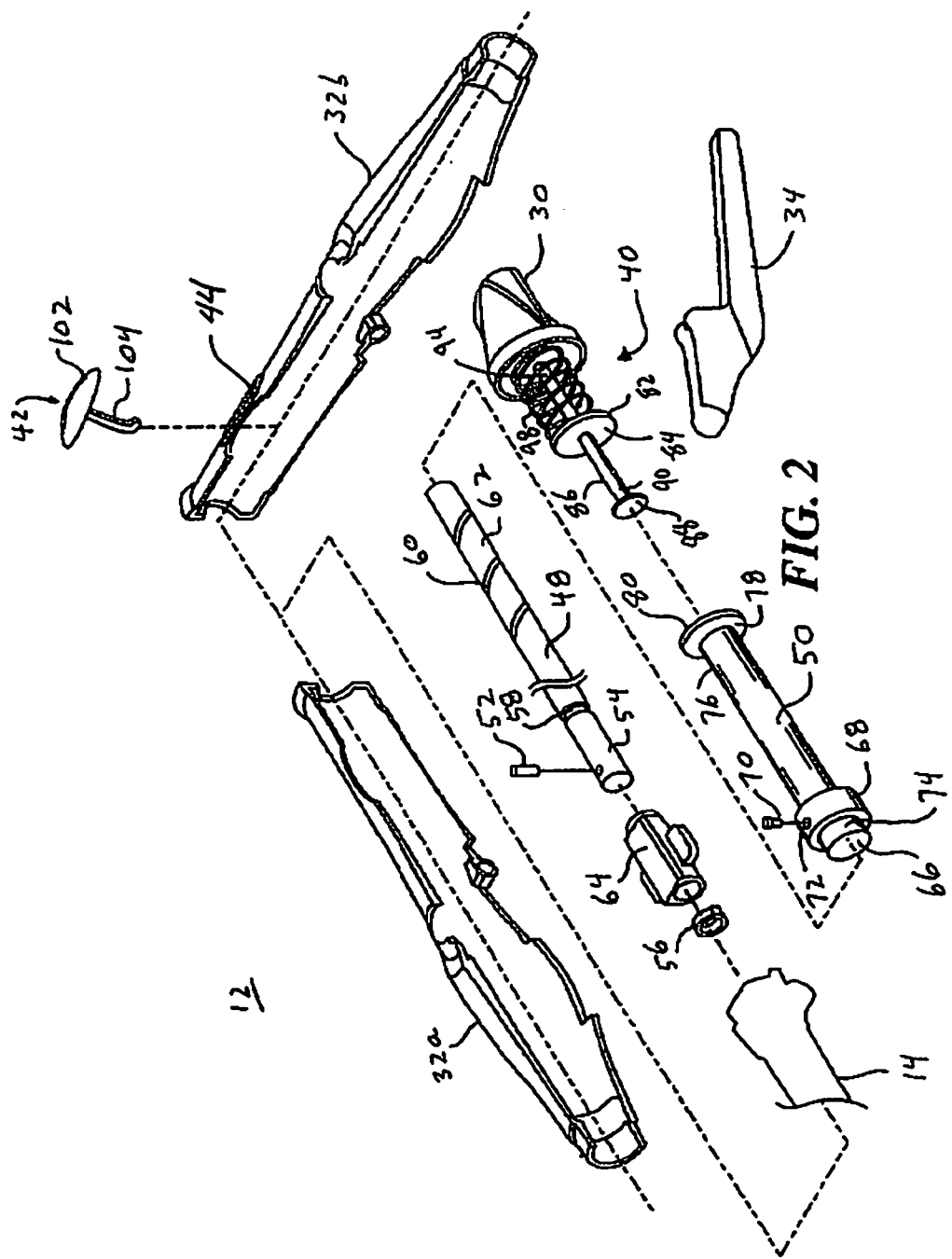
FIG. 2 is a perspective view, with parts separated, of a handle portion of the surgical stapler of FIG. 1.

Referring now to FIGS. 1 and 2, in order to move anvil assembly 22 relative to staple cartridge 20 in response to rotation of approximation knob 30 (FIG. 1), surgical stapling instrument 10 includes a drive screw 48 and a rotatable sleeve 50 mounted in body housing 32 of handle assembly 12. Drive screw 48 is longitudinally movable within body housing 32 and is connected to anvil retention shall 28. Drive screw 48 includes a pin 52, positioned through a distal end 54 of drive screw 48, which is directly or indirectly connected to the anvil retention shaft 28 in a known manner. For example, in order to transmit longitudinal motion through curved elongate body portion 14, pin 52 may be connected to proximal ends of bands (not shown) while distal ends of the bands may be connected to anvil retention shaft 28 in a manner described in more detail in U.S. Pat. No. 7,303,106, the disclosure of which is hereby incorporated by reference herein. Thus, longitudinal movement of drive screw 48 within body housing 32 effects longitudinal movement of anvil assembly 22 relative to staple cartridge 20.

As shown, body housing 32 is provided as complementary halves 32a and 32b. A seal 56 is provided in a circumferential groove 58 formed in distal end 54 of drive screw to prevent escape of insufflation gases and other fluids through elongate body portion 14 and out body housing 32. A screw stop 64 is provided on distal end 54 of drive screw 48 to limit the longitudinal travel of drive screw 48 within body housing 32. A helical groove 60 is provided in a proximal portion 62 of drive screw 48 and is engaged by rotatable sleeve 50 in order to move drive screw 48 longitudinally.

Specifically, drive screw 48 is positioned within a bore 66 formed within rotatable sleeve 50. An enlarged collar 68 rotatably supports rotatable sleeve 50 within body housing 32. In order to move drive screw 48 longitudinally within bore 66 of rotatable sleeve 50, a drive pin 70 extends through a hole 72 formed through enlarged collar 68 and extends into bore 66. Drive pin 70 rides within helical groove 60 formed in proximal portion 62 of drive screw 48. Thus, as rotatable sleeve 50 is rotated within body housing 32, drive pin 70 rides within helical groove 62 drawing and/or advancing drive screw 48 within body housing 32. As noted herein above, drive screw 48 is connected to anvil assembly 22. Longitudinal movement of drive screw 48 within body housing 32 effects longitudinal movement of anvil assembly 22 relative to staple cartridge 20.

As approximation knob 30 is rotated, rotational force or torque is applied to rotatable sleeve 50 to rotate rotatable sleeve 50 and move drive pin 70 within helical groove 60 in drive screw 48. The rotational force is converted to longitudinal or linear force moving anvil assembly 22 toward staple cartridge 20 thereby compressing tissue captured between anvil and staple cartridge in response to rotation of approximation knob 30.

In the absence of any control or limiting factors, as continued torque is applied to rotatable sleeve 50, an increasing amount of linear force is transmitted to, or exerted on, anvil assembly 22 thereby applying an increasing amount of compression to the tissue captured between anvil plate 24 of anvil assembly 22 and staple cartridge 20. In order to prevent over compression or under compression, torque limiting mechanism 40 is provided to limit the amount of torque applied to rotatable sleeve 50, and thus the amount of linear force applied to anvil assembly 22, to a predetermined or adjustable level.

Figure 3:
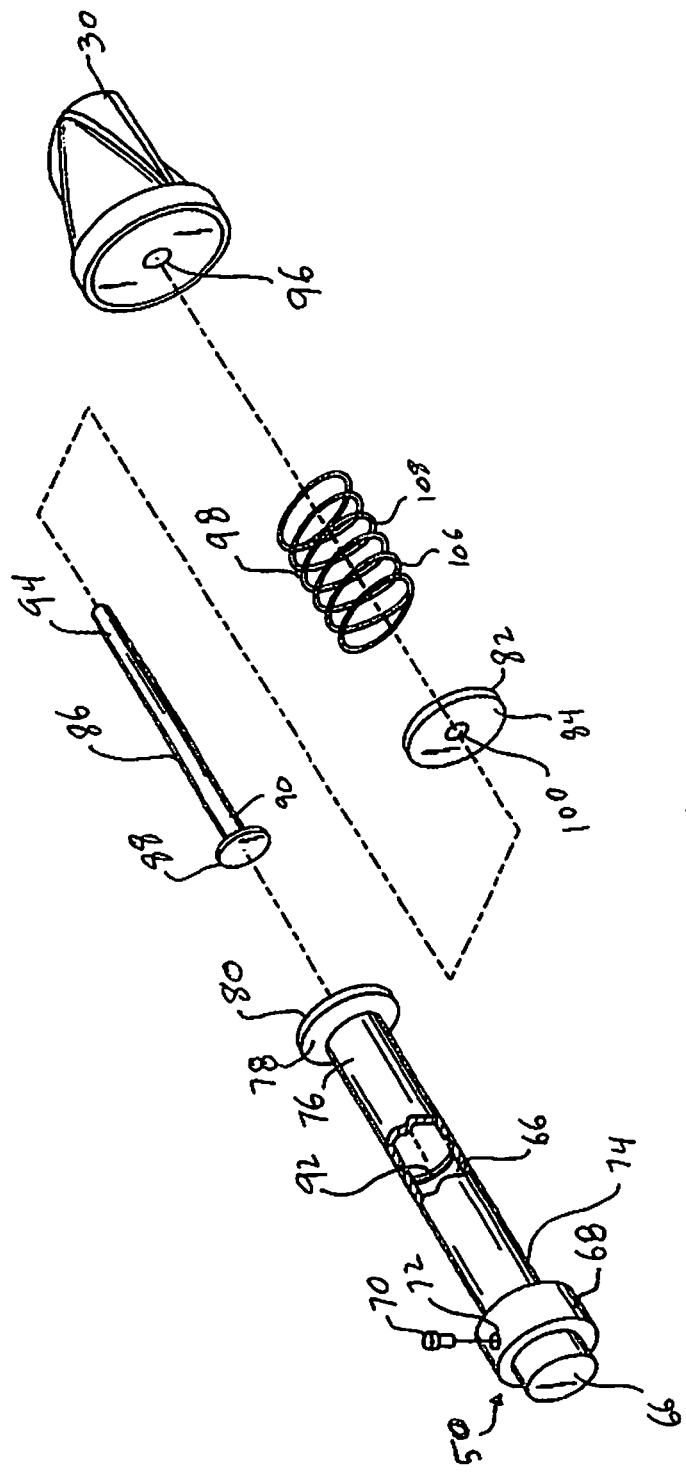
FIG. 3 is a perspective view, with parts separated, of a torque limiting mechanism utilized in the handle portion of FIG. 2.

Referring now to FIGS. 2 and 3, enlarged collar 68, which supports rotatable sleeve 50 within body housing 32 (FIG. 2) is located at a distal end 74 of rotatable sleeve 50. In order for the surgeon to manually rotate rotatable sleeve 50, a proximal end 76 of rotatable sleeve 50 is provided with a driven member or disk 78 having a driven surface 80. Driven disk 78 forms a part of torque limiting mechanism 40. As noted herein above, approximation knob 30 is provided on body housing 32 and is rotatable to affect movement of anvil assembly 22. As shown, torque limiting mechanism 40 is located between approximation knob 30 and rotatable sleeve 50. Torque limiting mechanism 40 is provided to limit the amount of rotational torque applied to rotatable sleeve 50 in order to control the amount of linear force, and thus tissue compression, applied to anvil assembly 22.

Referring to FIGS. 2, 3 and 4, in this embodiment, torque limiting mechanism 40 further includes a driving member or disk 82 having a driving surface 84. Driving surface 84 is provided to fictionally engage driven surface 80 of driven disk 78 in order to rotate rotatable sleeve 50. The driving member or disk 82 is also attached to the knob 30. Driving disk 82 is mounted on a drive shaft 86. Drive shaft 86 includes a support disk 88 provided at a distal end 90 of driveshaft 86. Support disk 88 is rotatably supported within a circumferential groove 92 formed in rotatable sleeve 50 (FIGS. 3 and 4). A proximal end 94 of driveshaft 86 is affixed to approximation knob 30. Specifically, proximal end 94 of drive shaft 86 is fixed within a hole 96 formed in approximation knob 30. Therefore, as approximation knob 30 is rotated, driving disk 82 of torque limiting mechanism 40 frictionally engages and rotates driven disk 78 of torque limiting mechanism 40 provided on rotatable sleeve 50.

Torque limiting mechanism 40 further includes a biasing spring 98 which is provided between approximation knob 30 and driving disk 82 to bias driving disk 82 into frictional engagement with driven disk 78. Drive shaft 86 extends through a hole 100 in driving disk 82. While not specifically shown, driving disk 82 is keyed (such as with a pin) or otherwise mounted on drive shaft 86 such that driving disk 82 rotates with drive shaft 86 and is free to move longitudinally along drive shall 86 in order to disengage from or slipped relative to driven disk 78.

As noted herein above, torque control 42 (FIGS. 1 and 2) is provided on body housing 32 to adjustably control the amount of compressive forces applied to tissue between staple cartridge 20 and anvil assembly 22. Referring for the moment to FIG. 2, torque control 42 includes a slide 102 which may be manually graspable and extend outside of body housing 32 to be located adjacent indicia plate 44. A member or hook 104 extends from slide 102 and engages coils such as, for example, coils 106, 108, etc., of biasing spring 98 to adjust the amount of spring pressure applied to driving disk 82. The torque control 42 adjusts the pressure applied by the driving member to the driven member. In this manner, torque control 42 is able to preset the maximum amount of pressure applied to driven member or disk 78 by driving member or disk 82. This pre-sets a maximum amount of torque to be applied to rotatable sleeve 50 and thus the maximum amount of compressive forces to be applied to tissue captured between staple cartridge 20 and anvil assembly 22.

It should be noted that, while torque limiting mechanism 40 includes a biasing spring 98 to bias driving disk 82 into engagement with driven disk 78, torque limiting mechanism 40 may omit biasing spring 98. In this configuration, driven surface 80 of driven disk 78 and driving surface 84 of driving disk 82 may be manufactured with predetermined coefficients of friction such that driving disk 82 slips relative to driven disk 78 at a predetermined torque limit.

Referring now to FIGS. 1, 2, 5 and 6, the use of torque limiting mechanism 40 to limit the amount of rotational force or torque applied to rotatable sleeve 50 will now be described. Referring initially to FIGS. 1 and 2, torque control 42 is adjusted such that hook 104 applies the desired amount of preload pressure to biasing spring 98. This is accomplished by a sliding slide 102 relative to indicia plate 44 until slide 102 is aligned with the appropriate numerical indicia 46 on indicia plate 44. Thereafter, approximation knob 30 is rotated in the direction of arrow A (FIG. 5) to draw anvil assembly 22 toward staple cartridge 20 thereby compressing first and second tissue sections T1 and T2 together and bring the tissue sections into position to be stapled.

Referring specifically to FIG. 5, rotation of approximation knob 30 in the direction of arrow A rotates driving disk 82 in the direction of arrow B. Driving disk 82's frictional engagement with driven disk 70 rotates driven disk 78 in the direction of arrow C thereby rotating rotatable sleeve 50 to compress the tissue sections as described hereinabove.

Referring now to FIG. 6, as approximation knob 30 continues to be rotated, the increasing compression of first and second tissue sections T1 and T2 requires an increasing amount of linear force passing through drive screw 48 and thus an increasing amount of rotational torque required by rotatable sleeve 50. At the predetermined amount of pressure applied by biasing spring 98 and controlled by torque control 42, the frictional forces between driven disk 78 and driving disk 82 are overcome allowing driving disk 82 to slip relative to driven disk 78. As driving disk 82 slips relative to driven disk 78, no further increasing amount of torque is applied to rotatable sleeve 50 and thus no further increasing amount of linear force is transmitted through drive screw 48 to anvil assembly 22. In this manner, torque limiting mechanism 40 prevent over compression of tissues captured between anvil assembly 22 and staple cartridge 20.

Referring now to FIGS. 7-9, and initially with regard to FIG. 7, there is disclosed an alternative embodiment of a torque limiting mechanism 110 for use with surgical stapling device 10 described herein above. Similar to torque limiting mechanism 40 described above, torque limiting mechanism 110 generally includes a driven member or disk 112 provided on proximal end 76 of rotatable sleeve 50 and a driving member or disk 114 mounted for longitudinal movement along a driveshaft 116. A biasing spring 118 is provided around drive shaft 116 and biases driving disk 114 into engagement with driven disk 112. Similar to driving disk 82 described herein above, driving disk 114 is mounted for rotational movement along with drive shaft 116 and is free to move longitudinally along drive shaft 116 against the bias of biasing spring 118.

A support disc 120 is provided on a distal end 122 of drive shaft 116 and is rotatably supported within circumferential groove 92 in rotatable sleeve 50. A proximal end 124 of drive shaft 116 is affixed within hole 96 in approximation knob 30. Thus, rotation of approximation knob 30 rotates drive shaft 116 and thus driving disk 114. In this embodiment, driven disk 112 is provided with a plurality of pawls or driven disk teeth 126 which are mechanically interengageable with a plurality of corresponding pawls or driving disk teeth 128 formed on driving disk 114. Driven disk teeth 126 and driving disk teeth 128 form respective driven and driving surfaces 130 and 132 on driven disk 112 and driving disk 114.

Referring now to FIGS. 8 and 9, in use, biasing spring 118 biases driving disk 114 into engagement with driven disk 112. Specifically, biasing spring 118 biases driving surface 132, including driving teeth 128, into engagement with driven surface 130, including driven teeth 126. In a manner identical to that described herein above, torque control 42 is manipulated to adjust the maximum amount of force applied by biasing spring 118 to driving disk 114. As approximation knob 30 is rotated, driving teeth 128 on driving disk 114 are interengaged with driven teeth 126 on driven disk 112 to thereby rotate rotatable sleeve 50. As further noted herein above, rotation of rotatable sleeve 50 effects longitudinal movement of anvil assembly 22 relative to staple cartridge 20 to thereby compress tissue.

With specific reference to FIG. 9, as rotatable sleeve 50 is rotated, an increasing amount of force is required to continue to rotate rotatable sleeve 50 due to the compressive forces existing between the tissues. Continued rotation of approximation knob 30 continues to apply torqued to rotatable sleeve 50 until such time as the amount of torque required exceeds the pressure applied to driving disk 114 by biasing spring 118. At this point, driving disk 114 "slips" relative to driving disk 112 and moves proximally in the direction of arrow D against the bias of biasing spring 118. Specifically, driving teeth 128 on driving disk 114 slip relative to or are disengaged from driven teeth 126 on driven disk 112 thereby preventing any further application of increased torque to rotatable sleeve 50. In this manner, torque limiting mechanism 110 prevents over compression of tissues captured between anvil assembly 22 and staple cartridge 20.

Referring now to FIGS. 10-12, and initially with regard to FIG. 10, there is disclosed a further alternative embodiment of a torque limiting mechanism 140 for use with surgical stapling device 10. Similar to torque limiting mechanism 40 described above, torque limiting mechanism 140 generally includes a driven member or disk 142 provided on proximal end 76 of rotatable sleeve 50 and a cone shaped driving member or disk 144 mounted for longitudinal movement along a drive shaft 146. A biasing spring 148 is provided around drive shaft 146 and biases driving disk 144 into engagement with driven disk 142. Similar to driving disk 82 described herein above, driving disk 144 is mounted for rotational movement along with drive shaft 146 and is free to move longitudinally along drive shaft 146 against the bias of biasing spring 148.

A support disc 150 is provided on a distal end 152 of drive shaft 146 and is rotatably supported within circumferential groove 92 in rotatable sleeve 50. A proximal end 154 of driveshaft 146 is affixed within hole 96 in approximation knob 30. Thus, rotation of approximation knob 30 rotates drive shaft 146 and thus driving disk 144. In this embodiment, driven disk 142 includes a driven disk surface 156 and driving disk 144 includes a driving disk surface 158. At least one releasable connector 160 is provided between driven disk surface 156 and driving disk surface 158. Releasable connector 160 slips relative to driven disk surface 156 and\or driving disk surface 158 when a preset amount of torque is applied to rotatable sleeve 50.

In this specific embodiment, releasable connectors 160 arc in the form of a plurality of connecting balls 162. Driven disk surface 156 of driven disk 142 includes a plurality of driven disk cups 164 and driving disk surface 158 of driving disk 144 includes a plurality of corresponding driving disk cups 166. Connecting balls 162 are movably supported between driven disk cups 164 and driving disk cups 166. Connecting balls 162 are maintained between driving disk cups 164 and driven disk cups 166 by the biasing pressure of biasing spring 148 on driving disk 144.

Referring now to FIGS. 11 and 12, in use, approximation knob 30 is rotated such that driving disk 144 rotates driven disk 142 through connecting balls 162. Rotation of driven disk 142 correspondingly rotates rotatable sleeve 50 thereby effecting longitudinal movement between anvil assembly 22 and staple cartridge 20 (FIG. 1). As anvil assembly 22 moves towards staple cartridge 20 to compress the tissues there between, an increasing amount of rotational force or torque is required to be applied to rotatable sleeve 50.

As best shown in FIG. 12, an increasing amount of rotational force is required to be applied to approximation knob 30 to continue rotation of rotatable sleeve 50. When the force needed to continue rotation a rotatable sleeve 50 exceeds that preset by torque control 42, driving disk 144 moves proximally against the bias of biasing spring 148. This causes connecting balls 162 to slit or "pop" out of driving disk cups 166 thereby removing any further rotational force applied to driven disk 142. Alternatively, while not specifically shown, connecting balls 162 may be firmly affixed within driving disk cups 166 in driving disk 144 such that releasable connecting balls 162 slip or pop out of driven disk cups 164 in driven disk 142 as driving disk 144 moved proximally against the pressure of biasing spring 140. In this manner, torque limiting mechanism 140 prevents over compression of tissues captured between anvil assembly 22 and staple cartridge 20 of surgical stapling device 10.

In further embodiments of the present disclosure, the body housing and handle assembly can incorporate a motorized actuator and may he connected to, or incorporate therein, a power source. An example of a powered, motorized device is disclosed in International Publication No. WO 09/039506 and U.S. Pat. No. 7,032,798, the disclosures of which are hereby incorporated by reference herein, in their entirety. The manually powered device discussed above converts the pivoting motion of the handle into linear motion of the anvil retention shaft. A motorized device can generate rotational motion, which is then converted to linear motion for clamping tissue, firing staples, and/or cutting tissue.

It will be understood that various modifications may be made to the embodiments disclosed herein. For example, alternative disconnecting mechanisms may be provided such as, for example, multiple friction plates, magnetic engagement mechanisms, etc. Further, the disclosed torque limiting mechanisms may find application in any surgical instrumentation incorporating tissue compression structure. Additionally, the disclosed torque limiting mechanisms may be provided as modular and interchangeable components having differing ranges of engagement pressures for use in surgical instruments. In addition, one or more removable adapters having an elongate shaft extending from the handle assembly to the distal end of the device can be used. Such adapters can have flexible shafts, curved, or other shapes, and may be designed to connect to various end effectors. Such adapters can also be designed to be connected to a manually driven handle assembly, a motorized actuator, or both. An adapter is disclosed in U.S. Pat. No. 7,922,063, the disclosure of which is hereby incorporated by reference herein, in its entirety. Therefore, the above description should not be construed as limiting, but merely as exemplifications of particular embodiments. Those skilled in the art will envision other modifications within the scope and spirit of the claims appended hereto.

The invention claimed is:

1. A torque limiting mechanism for use in a surgical instrument that compresses tissue, comprising:
  a driven member engageable with an approximating mechanism of the surgical instrument, the driven member having a driven surface;
  a driving member having a driving surface engageable with the driven surface of the driven member and connected to a clamping actuator of the surgical instrument, the driving member rotatable relative to the driven member, such that the driving surface of the driving member slips relative to the driven surface of the driven member at a predetermined engagement pressure;
  a biasing spring engageable with the driving member such that the driving member is spring biased into engagement with the driven member; and
  a torque control selectively adjusting the pressure applied by the driving member to the driven member, the torque control including a hook selectively engageable with the biasing spring, and a slide member operatively coupled with the hook.

2. The torque limiting mechanism as recited in claim 1, wherein the driving surface frictionally engages the driven surface.

3. The torque limiting mechanism as recited in claim 1, wherein the driving surface and the driven surface have an interengaging structure.

4. The torque limiting mechanism as recited in claim 3, wherein the interengaging structure includes interengaging teeth.

5. The torque limiting mechanism as recited in claim 3, wherein the interengaging structure is a detent mechanism.

6. The torque limiting mechanism as recited in claim 5, further comprising at least one movable connector between the driving surface and the driven surface.

7. The torque limiting mechanism as recited in claim 5, wherein the detent mechanism includes cups positioned on one of the driving surface and the driven surface and balls positioned on the other one of the driving surface and the driven surface removably engageable with the cups.

* * * * *